United States Patent
Baltekin et al.

(10) Patent No.: US 12,233,418 B2
(45) Date of Patent: Feb. 25, 2025

(54) CELL CAPTURE IN MICROFLUIDIC DEVICES

(71) Applicant: ASTREGO DIAGNOSTICS AB, Uppsala (SE)

(72) Inventors: Özden Baltekin, Uppsala (SE); Ove Öhman, Uppsala (SE); Martin Lovmar, Mölndal (SE); Johan Elf, Uppsala (SE); Mikael Olsson, Uppsala (SE)

(73) Assignee: ASTREGO DIAGNOSTICS AB, Uppsala (SE)

( * ) Notice: Subject to any disclaimer, the term of this patent is extended or adjusted under 35 U.S.C. 154(b) by 1200 days.

(21) Appl. No.: 16/969,891

(22) PCT Filed: Feb. 15, 2019

(86) PCT No.: PCT/SE2019/050135
§ 371 (c)(1),
(2) Date: Aug. 13, 2020

(87) PCT Pub. No.: WO2019/160492
PCT Pub. Date: Aug. 22, 2019

(65) Prior Publication Data
US 2021/0008554 A1   Jan. 14, 2021

(30) Foreign Application Priority Data
Feb. 16, 2018   (SE) .................... 1850169-2

(51) Int. Cl.
*B01L 3/00*   (2006.01)
*B01D 61/18*   (2006.01)
(Continued)

(52) U.S. Cl.
CPC ........ *B01L 3/502761* (2013.01); *B01D 61/18* (2013.01); *B01D 63/005* (2013.01);
(Continued)

(58) Field of Classification Search
CPC ...... B01D 61/14; B01D 61/18; B01D 63/005; B01L 3/502715; B01L 3/502746;
(Continued)

(56) References Cited

U.S. PATENT DOCUMENTS 10,913,969 B2   2/2021   Elf et al.
2004/0072278 A1   4/2004   Chou et al.
(Continued)

FOREIGN PATENT DOCUMENTS

JP   2017-519517 A   7/2017
WO   2006/079007 A2   7/2006
(Continued)

OTHER PUBLICATIONS

Baltekin, Özden et al., Antibiotic susceptibility testing in less than 30 min using direct single-cell imaging, PNAS, vol. 114, No. 34, pp. 9170-9175 (Aug. 22, 2017).
(Continued)

*Primary Examiner* — Matthew D Krcha
*Assistant Examiner* — Austin Q Le
(74) *Attorney, Agent, or Firm* — Porter Wright Morris & Arthur LLP

(57) ABSTRACT

A capturing of target cells from a biological sample is achieved by inducing a flow of the biological sample in a flow channel (30, 60) of an upstream microfluidic device (1). Target cells present in the biological sample are captured in cell channels (20) of the upstream microfluidic device (1). Once at least a minimum number of target cells are captured in the cell channels (20), the flow of the biological sample in the flow channel is reduced and are verse flow is applied at the upstream microfluidic device (1) to release the target cells captured in the cell channels (20) of the upstream (Continued)

microfluidic device (1) and enable transfer the target cells into cell channels (120) of a downstream microfluidic device (100).

11 Claims, 9 Drawing Sheets

(51) Int. Cl.
  *B01D 63/00* (2006.01)
  *G01N 33/50* (2006.01)
(52) U.S. Cl.
  CPC ... *B01L 3/502715* (2013.01); *B01L 3/502746* (2013.01); *G01N 33/5008* (2013.01); *B01L 2200/027* (2013.01); *B01L 2200/0652* (2013.01); *B01L 2200/10* (2013.01); *B01L 2300/0627* (2013.01); *B01L 2300/0681* (2013.01); *B01L 2300/0861* (2013.01); *B01L 2400/082* (2013.01)
(58) Field of Classification Search
  CPC ......... B01L 3/502753; B01L 3/502761; B01L 2200/027; B01L 2200/0652; B01L 2200/0668; B01L 2200/10; B01L 2300/0627; B01L 2300/0681; B01L 2300/0816; B01L 2300/0861; B01L 2300/0864; B01L 2300/088; B01L 2400/082; B01L 2400/086; G01N 15/1023; G01N 15/1031; G01N 15/1433; G01N 15/1459; G01N 15/147; G01N 15/1484; G01N 33/5008; G01N 33/54366; G01N 33/569; G01N 2001/4088; G01N 2015/1006; G01N 2015/1486
  See application file for complete search history.

(56) References Cited

U.S. PATENT DOCUMENTS

| | | | |
|---|---|---|---|
| 2009/0101559 A1* | 4/2009 | Bala Subramaniam | B01D 61/18 210/194 |
| 2013/0330767 A1 | 12/2013 | Liddell et al. | |
| 2013/0337500 A1 | 12/2013 | Tan et al. | |
| 2014/0087456 A1 | 3/2014 | Lim et al. | |
| 2015/0300939 A1* | 10/2015 | Ma | G01N 15/10 435/287.1 |
| 2016/0296932 A1 | 10/2016 | Tan | |
| 2017/0137861 A1* | 5/2017 | Elf | C12Q 1/6874 |
| 2019/0168221 A1* | 6/2019 | Sollier | B01L 3/502738 |
| 2021/0197196 A1* | 7/2021 | Glieberman | C12M 23/16 |

FOREIGN PATENT DOCUMENTS

| | | | |
|---|---|---|---|
| WO | 2013/019491 A1 | 2/2013 | |
| WO | 2016/007063 A1 | 1/2016 | |
| WO | WO-2016007068 A1 * | 1/2016 | ........ B01L 3/502761 |
| WO | 2016/207320 A1 | 12/2016 | |

OTHER PUBLICATIONS

Wang, Ping et al., Robust Growth of Escherichia coli, Current Biology, vol. 20, pp. 1099-1103 (Jun. 22, 2010).
Iwai, Kosuke et al., A resettable dynamic microarray device, Biomed Microdevices, vol. 13, pp. 1089-1094 (2011).
Beattie, William et al., Clog-free cell filtration using resettable cell traps, Lab Chip, vol. 14, pp. 2657-2665 (2014).
Office Action from Corresponding Chinese Application No. 201980007568.7 dated Feb. 15, 2023.
Office Action from corresponding Japanese Application No. 2020-53887 dated Jan. 13, 2023, with English Translation.
Search Report from corresponding Japanese Application No. 2020-538887 dated Dec. 28, 2022, with English Translation.

* cited by examiner

CELL CAPTURE IN MICROFLUIDIC DEVICES

TECHNICAL FIELD

The present invention generally relates to microfluidic devices, and in particular to capturing target cells from biological samples in such microfluidic devices.

BACKGROUND

The recent development in single cell biology has made it clear that isogenic cells can display large differences in gene expression and behavior also when grown under identical conditions. New devices are thereby needed to characterize cell-to-cell differences in phenotypes over time. Such devices need to meet certain criteria in order to be an effective tool in culturing and monitoring single cells. For instance, these devices should be easy to load with cells so that one can monitor phenotypic characteristics immediately after loading. Furthermore, many different individual cells need to be grown in parallel to characterize the cell-to-cell differences and to overcome measurement errors in the characterization of individual cells by averaging. The devices should be designed to enable culturing of cells for a long period of time under constant and well-controlled growth conditions to monitor, for example, linage dependent dynamics. It is further preferred if the devices enable change of culturing conditions to monitor dynamic changes in response to new culture media or test agents. For instance, it could be advantageous to test different culture media on isogenic cells in parallel or monitor the response to media changes on different cell strains in parallel.

A desired application of microfluidic devices is to rapidly and in parallel monitor the phenotypic response of target cells, such as bacteria, in a biological sample to a set of antibiotics or other test agents immediately after the target cells have been loaded in the microfluidic device. In such an application, it would be advantageous to be able to directly load the microfluidic device with the biological sample to gain speed in the analysis.

A prior art microfluidic device, denoted the "Mother Machine", is disclosed in Wang et al., Current Biology 2010, 20: 1099-1103. The Mother Machine allows for monitoring cells in many different cell channels in parallel. However, this prior art microfluidic device has several shortcomings. For instance, cell loading is complicated and it is hard to rapidly change culture conditions in the microfluidic device.

Further microfluidic devices that are useful for analysis of biological samples are shown in WO 2016/007063 and WO 2016/007068.

Baltekin et al., PNAS 2017, 114(34): 9170-9175 discloses a fast antibiotic susceptible testing (AST) test, FASTest, using a microfluidic device.

Many biological samples comprising target cells to be analyzed in microfluidic devices additionally comprise contaminating particles, such as other cells, and/or comprising the target cells in comparatively low concentrations as compared to contaminating particles. This may complicate analysis and characterization of the target cells since the contaminating particles will outcompete the target cells during cell capture and may interfere with the analysis and characterization.

SUMMARY

It is a general objective to provide an efficient capture of target cells from a biological sample into a microfluidic device.

This and other objectives are met by embodiments as disclosed herein.

An aspect of the embodiments relates to a method of capturing target cells from a biological sample. The method comprises inducing a flow of a biological sample comprising target cells in a flow channel of an upstream microfluidic device between a first end and a second end of the flow channel. The upstream microfluidic device comprises a substrate having cell channels adapted to accommodate the target cells, a flow input channel having a first end and a second end and a flow output channel in fluid connection with a fluid port. A respective first end of the cell channels is in fluid connection with the flow input channel and a respective second end of the cell channels is in fluid connection with the flow output channel. The cell channels comprise a respective obstruction designed to prevent the target cells from passing the respective obstruction and into the flow output channel. The method also comprises monitoring the cell channels to detect presence of target cells captured in the cell channels. When at least a minimum number of target cells are captured in the cell channels, the flow of the biological sample in the flow channel is reduced and a fluid medium is applied at the fluid port of the upstream microfluidic device to release the target cells captured in the cell channels of the upstream microfluidic device and enable transfer of the target cells into cell channels of a downstream microfluidic device. The downstream microfluidic device comprises a substrate having cell channels adapted to accommodate the target cells, a flow input channel having a first end and a second end and a flow output channel in fluid connection with a fluid port. A respective first end of the cell channels is in fluid connection with the flow input channel and a respective second end of the cell channels is in fluid connection with the flow output channel. The cell channels comprise a respective obstruction designed to prevent the target cells from passing the respective obstruction and into the flow output channel.

Another aspect of the embodiments relates to a system for capturing target cells from a biological sample. The system comprises an upstream microfluidic device, a downstream microfluidic device, a fluid connector and a flow controller. The upstream microfluidic device comprises a substrate having cell channels adapted to accommodate the target cells, a flow input channel having a first end and a second end and a flow output channel in fluid connection with a fluid port. A respective first end of the cell channels is in fluid connection with the flow input channel and a respective second end of the cell channels is in fluid connection with the flow output channel. The cell channels comprise a respective obstruction designed to prevent the target cells from passing the respective obstruction and into the flow output channel. The downstream microfluidic device comprises a substrate having cell channels adapted to accommodate the target cells, a flow input channel having a first end and a second end and a flow output channel in fluid connection with a fluid port. A respective first end of the cell channels is in fluid connection with the flow input channel and a respective second end of the cell channels is in fluid connection with the flow output channel. The cell channels comprise a respective obstruction designed to prevent the target cells from passing the respective obstruction and into the flow output channel. The flow controller is adapted to induce a flow of the biological sample comprising the target cells in a flow channel of the upstream microfluidic device between a first end and a second end of the flow channel. The fluid connector is adapted to interconnect, when at least a minimum number of target cells are captured in the cell channels of the upstream microfluidic device, the first end and/or the second end of the flow input channel of the upstream microfluidic device to the first end and/or the second end of the flow input channel of the downstream microfluidic device. The flow controller is adapted to, when at least a minimum number of target cells are captured in the cell channels of the upstream microfluidic device, reduce the flow of the biological sample in the flow channel and apply a fluid medium at the fluid port of the upstream microfluidic device to release the target cells captured in the cell channels of the upstream microfluidic device and transfer the target cells into the cell channels of the downstream microfluidic device.

The present embodiments enable an efficient capturing of target cells from a biological sample by interconnecting two microfluidic devices. The upstream microfluidic device then enables an enrichment of target cells by separating the target cells from contaminating particles that may also be present in the biological sample. In addition, culturing of the target cells can take place in the upstream microfluidic device while the biological sample is flown therethrough. Once a sufficient number of target cells has been reached these target cells are released from the upstream microfluidic device and transferred by a reverse fluid flow into the downstream microfluidic device. The target cells captured in the downstream microfluidic device may then be characterized with a low risk of contaminating particles that otherwise may interfere with the characterization.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
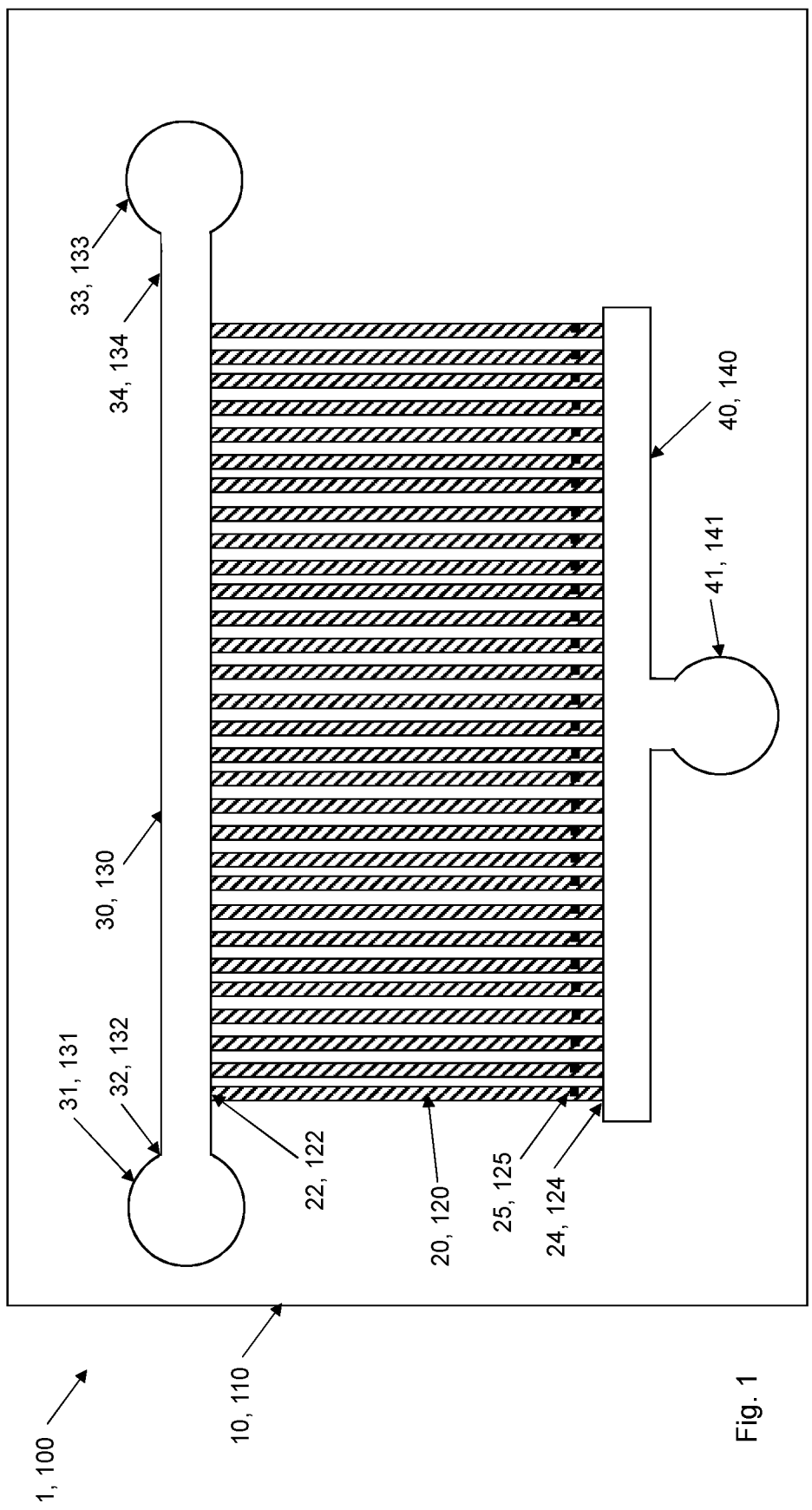
FIG. 1 is a schematic illustration of a microfluidic device according to an embodiment.

Throughout the drawings, the same reference numbers are used for similar or corresponding elements.

The present invention generally relates to microfluidic devices, and in particular to capturing target cells from biological samples in such microfluidic devices.

Microfluidic devices have been proposed to analyze and monitor target cells present in a biological sample to determine various characteristics of the target cells, such as phenotypic and/or genotypic characteristics and traits. This approach generally works well in the case of substantially pure biological samples mainly comprising the target cells in a liquid medium, or if the biological sample comprises the target cells at a comparatively high concentration.

However, in several applications the biological sample can be complex, additionally comprising so-called contaminating particles and/or comprising the target cells at a comparatively low concentration. The contaminating particles could include cells other than the target cells, cell debris and non-cell material, such as dust and/or dirt particles. In these applications, the contaminating particles may clog the microfluidic device thereby preventing efficient capture of the target cells present in the biological sample in the microfluidic device. Furthermore, if the biological sample comprises comparatively higher concentrations of the contaminating particles as compared to the target cells, the contaminating particles may outcompete the target cells during the capture in the microfluidic device with the consequence of not capturing any or too few target cells in the microfluidic device. In either case, there will not be sufficient number of target cells captured in the microfluidic device in order to make an efficient analysis of the target cells and determine the characteristics thereof.

A typical situation would be a blood sample taken from a (tentative) sepsis patient. In such a case, the blood sample most often comprises a comparatively low concentration of infection-causing bacteria as target cells and comparatively much higher concentrations of white blood cells (WBCs) and red blood cells (RBCs) as contaminating particles.

This means that if such a blood sample is loaded into a microfluidic device the WBCs and RBCs may obstruct and clog cell channels in the microfluidic device and/or occupy substantially all cell channels, in which the bacteria should be captured. As a consequence, no or far too few bacteria will be captured in the microfluidic device with such a blood sample.

There is therefore a need for an efficient capturing of target cells from a biological samples in a microfluidic device.

This objective is solved according to the present embodiments by having, see FIGS. 1-6, multiple, i.e., at least two, microfluidic devices 1, 100 including at least one first microfluidic device, denoted upstream microfluidic device 1 herein, and at least one second microfluidic device, denoted downstream microfluidic device 100 herein. In such a case, a biological sample comprising target cells, such as target cells at a low concentration and/or additionally comprising contaminating particles, is input to the upstream microfluidic device 1 in order to capture target cells in cell channels 20, also denoted cell traps, of the upstream microfluidic device 1. This capturing is generally taking place over an extended period of time during which a flow of the biological sample is induced in a flow channel 30, 60 of the upstream microfluidic device 1. This flow induction provides opportunities for target cells in the biological sample to enter and be captured in cell channels 20. Furthermore, target cells present in the biological sample flowing through the flow channel 30, 60 may grow and multiply during this flow induction phase to increase the number of target cells and thereby increase the chances of capturing a sufficient number of the target cells in the cell channels 20. Also, target cell already captured in the cell channels 20 will multiply and propagate in the cell channels 20 during the flow induction phase, thereby increasing the total number of captured target cells.

Figure 4:
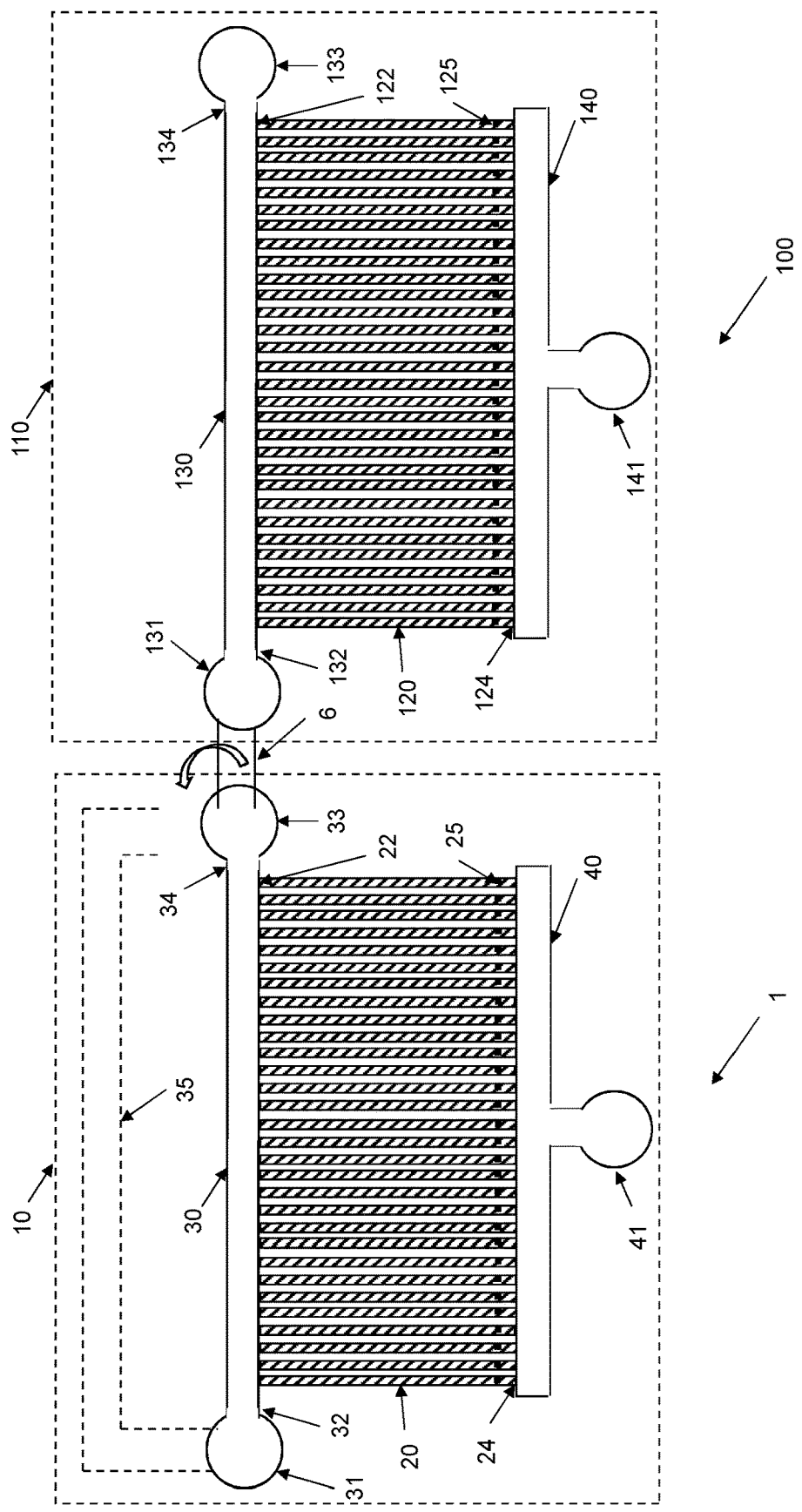
FIG. 4 is a schematic illustration of a system comprising upstream and downstream microfluidic devices according to an embodiment.

Once a sufficient number of target cells has been captured in the cell channels 20 of the upstream microfluidic device 1, the flow of the biological sample in the flow channel 30, 60 is reduced, such as interrupted, and the upstream microfluidic device 1 is optionally connected to the downstream microfluidic device 100, which is schematically illustrated in FIG. 4. A reverse flow is then applied in the upstream microfluidic device 1 to release the target cells captured in the cell channels 20 of the upstream microfluidic device 1 and to enable capture of the target cells in cell channels 120 of the downstream microfluidic device 100.

The upstream microfluidic device 1 thereby has several important functions to achieve an efficient capturing of the target cells. Firstly, it enriches target cells from the biological sample by removing contaminating particles. Thus, the cell channels 20 and the flow induction are designed and adapted to mainly capture target cells, while contaminating particles are filtered away. Accordingly, a purification and enrichment of target cells takes place in the upstream microfluidic device 1. Secondly, the flow induction phase in the upstream microfluidic device 1 provides opportunities for target cells in the biological sample and target cells captured in the cell channels 20 to grow and multiply, thereby increasing the number of target cells. Thirdly, the initial capture of target cells in the upstream microfluidic device 1 followed by the release and subsequent capture of the target cells in the downstream microfluidic device 100 achieves a concentration of the target cells in fluid medium. Thus, although the initial concentration of target cells in the biological sample may be low, the enrichment obtained according to the invention significantly increases the concentration of the target cells in the downstream microfluidic device 100.

The present embodiments thereby enable capturing of sufficient number of target cells in the downstream microfluidic device 100 in order to make an efficient analysis of the target cells and determine characteristics thereof even if the original biological sample contained a low concentration of the target cells and/or a lot of contaminating particles.

Figure 8:
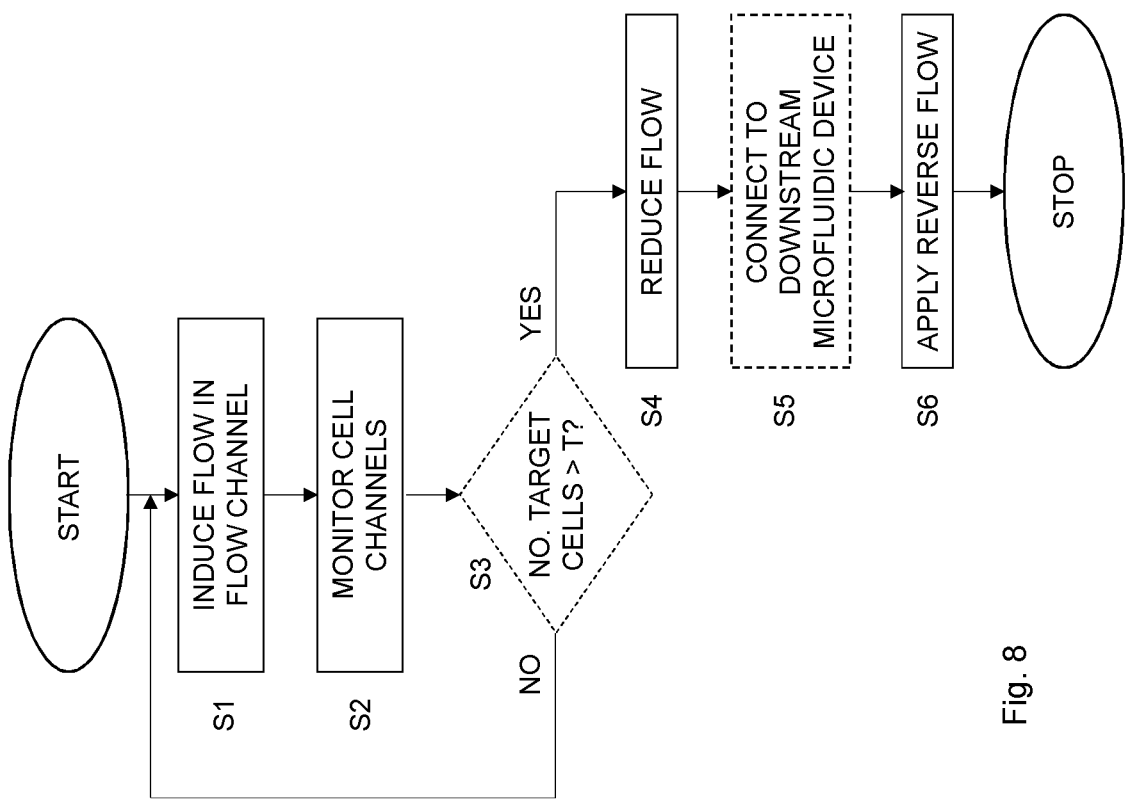
FIG. 8 is a flow chart illustrating a method of capturing target cells according to an embodiment.

FIG. 8 is a flow chart illustrating a method of capturing target cells from a biological sample according to an embodiment. The method comprises inducing, in step S1, a flow of a biological sample comprising target cells in a flow channel 30, 60 of an upstream microfluidic device 1 between a first end 32, 62 and a second end 34, 64 of the flow channel 30, 60. The upstream microfluidic device 1 comprises a substrate 10 having cell channels 20 adapted to accommodate the target cells. The upstream microfluidic device 1 also comprises a flow input channel 30 having a first end 32 and a second end 34 and a flow output channel 40 in fluid connection with a fluid port 41. A respective first end 22 of the cell channels 20 is in fluid connection with the flow input channel 30 and a respective second end 24 of the cell channels 20 is in fluid connection with the flow output channel 40. The cell channels 20 comprise a respective obstruction 25 designed to prevent or at least restrict or inhibit the target cells 20 from passing the respective obstruction and into the flow output channel 40.

The method also comprises monitoring, in step S2, the cell channels 20 to detect presence of target cells captured in the cell channels 20.

This monitoring in step S2 could be performed serially or at least partly in parallel with step 51. In the former case, the flow induction in the flow channel 30, 60 may be temporarily interrupted during the monitoring of the cell channels 20 in step S2. If the monitoring in step S2 concludes, see optional step S1, that there are not sufficient number of target cells in the cell channels 20, the method continues to step S1 to thereby resume the flow of the biological sample in the flow channel 30, 60.

In the latter case, the monitoring of cell channels 20 in step S2 takes place while the biological sample is flown in the flow channel 30, 60. The monitoring in step S2 could then be performed once or at multiple time instances, such as scheduled or regular time instances, for instance every 30 s, every minute, every second minute, etc. It is also possible to have a more or less continuous monitoring of the cell channels 20 in step S2 instead of once or at multiple time instances.

In either case, when the monitoring in step S2 concludes that at least a minimum number of target cells are captured in the cell channels 20, the method continues to step S4. This is schematically illustrated in FIG. 8 as the case when the number of detected target cells in the cell channels 20 exceeds some predefined value T. This value and thereby the minimum number of target cells is typically defined in advance and generally depends on the type of subsequent processing of the target cells, such as characterization of the target cells that may be performed in the downstream microfluidic device 100.

As long as the monitoring in step S2 determines that there are not sufficient number of detected target cells in the cell channels 20 the loop of steps S1 and S2 is continued by inducing the flow of the biological sample in the flow channel 30, 60 and monitoring the cell channels 20.

When it is determined that at least a minimum number of target cells are captured in the cell channels 20, the method continues to step S4. This step S4 comprises reducing the flow of the biological sample in the flow channel 30, 60. A next step S6 comprises applying a fluid medium at the fluid port 41 of the upstream microfluidic device 1 to release the target cells captured in the cell channels 20 of the upstream microfluidic device 1 and enable transfer of the target cells into cell channels 120 of a downstream microfluidic device 100.

The downstream microfluidic device 100 comprises a substrate 110 having cell channels 120 adapted to accommodate the target cells. The downstream microfluidic device 100 also comprises a flow input channel 130 having a first end 132 and a second end 134 and a flow output channel 140 in fluid connection with a fluid port 141. A respective first end 122 of the cell channels 120 is in fluid connection with the flow input channel 130 and a respective second end 124 of the cell channels 120 is in fluid connection with the flow output channel 140. The cell channels 120 comprise a respective obstruction 125 designed to prevent or at least restrict or inhibit the target cells 120 from passing the respective obstruction and into the flow output channel 140.

Thus, flow of the biological sample is reduced, such as fully interrupted or stopped or at least reduced in comparison to the flow induced in step S1, once sufficient number of target cells are captured and present in the cell channels 20 in the upstream microfluidic device 1.

A reverse fluid flow is then applied at the upstream microfluidic device 1. This means that the fluid flow is input at the fluid port 41 of the flow output channel 40 and that the applied fluid medium flows into the flow output channel 40, through the cell channels 20 and into the flow input channel 30 of the upstream microfluidic device 1. When the fluid medium passes through the cell channels 20 it transfers the target cells captured in these cell channels 20 with the flow, bringing the target cells into the flow input channel 30.

In an embodiment, the method also comprises step S5 as shown in FIG. 8. This step S5 comprises connecting the first end 32 and/or the second end 34 of the flow input channel 30 of the upstream microfluidic device 1 to the first end 132 and/or the second end 134 of the flow input channel 130 of the downstream microfluidic device 100. The flow input channels 30, 130 of the two microfluidic devices 1, 100 are then interconnected to provide a fluid path from the flow input channel 30 of the upstream microfluidic device 1 to the flow input channel 130 of the downstream microfluidic device 100.

In this embodiment, the reverse flow carrying the target cells continues from the flow input channel 30 of the upstream microfluidic device 1 into the flow input channel 130 of the downstream microfluidic device 100, through the cell channels 120, and into the flow output channel 140 and out through the fluid port 141 of the downstream microfluidic device 100. The target cells transferred by this reverse flow are captured in cell channels 120 of the downstream microfluidic device 100 due to the presence of the respective obstructions 125.

The captured target cells in the cell channels 120 of the downstream microfluidic device 100 can then be further processed or characterized. For instance, the target cells could be characterized with regard to phenotype and/or genotype, classified or identified, etc.

The fluid medium applied in step S6 could be any fluid or liquid medium that is compatible with the target cells. For instance, the fluid medium could be a culture medium.

In a preferred embodiment, at least one of the ends 32, 34 of the flow input channel 30 in the upstream microfluidic device 1 is connected to at least one of the ends 132, 134 of the flow input channel 130 in the downstream microfluidic device 100. This fluid connection is preferably implemented by a fluid interconnector 6. The fluid interconnector 6 could for instance be a tubing that is connected to respective fluid ports 31, 33, 131, 133 of the flow input channels 30, 130. Alternatively, the fluid interconnector 6 could be a channel defined in the substrate 10, 110 that is blocked, such as by a valve, during steps S1 and S2, and then opened in step S5 to provide the fluid connection between ends 32, 34, 132, 134 of the flow input channels 30, 130.

Figure 7:
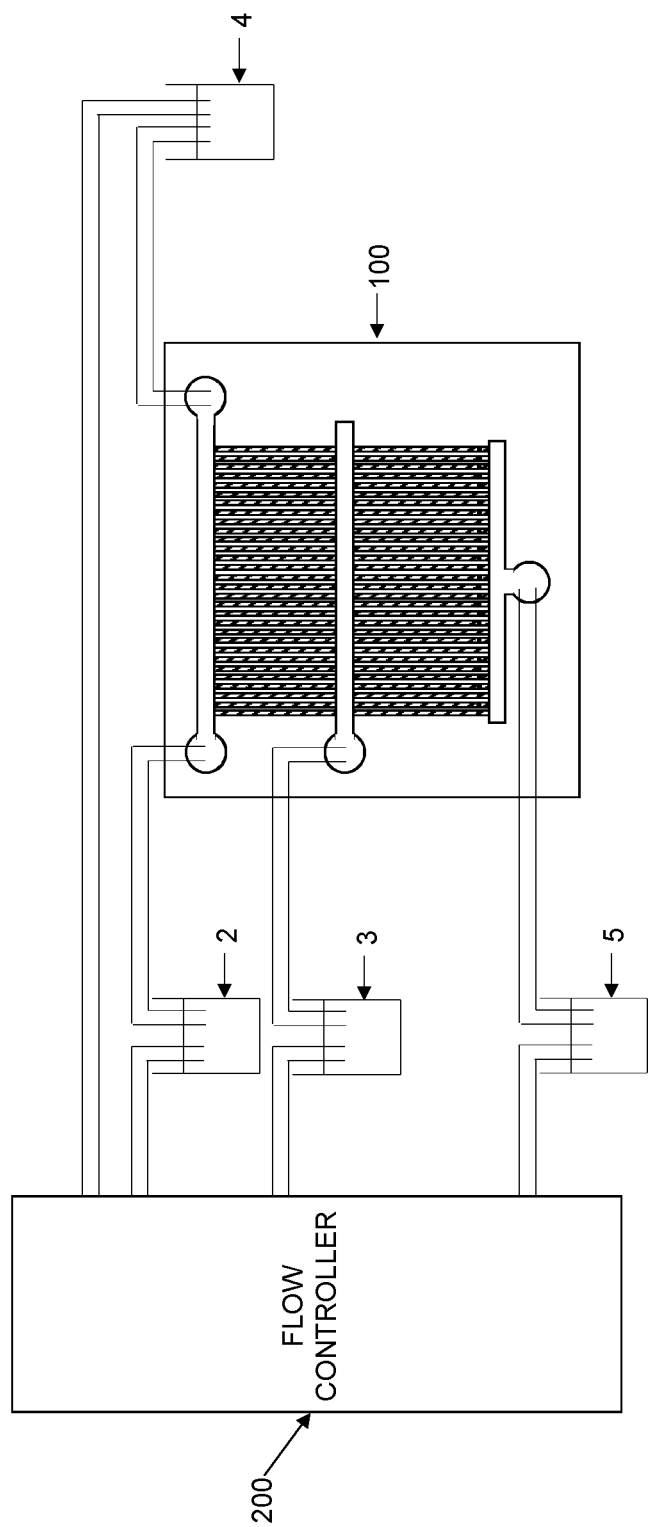
FIG. 7 schematically illustrates a flow controller with fluid reservoirs connectable to fluid ports of a microfluidic device according to an embodiment.

Although a fluid interconnector 6 is preferred to enable transfer of target cells between the cell channels 20 in the upstream microfluidic device 1 and the cell channels 120 of the downstream microfluidic device 100, the embodiments are not limited thereto. For instance, the reverse flow applied in step S6 could transfer target cells captured in cell channels 20 of the upstream microfluidic device 1 towards one of the ends 32, 34 of the flow input channel 30. As shown in FIG. 1, the respective end 32, 34 is preferably connected to a fluid port 31, 33. The fluid port 31, 33 could then itself be designed to operate as a fluid reservoir or is connected to a fluid reservoir 3 as shown in FIG. 7. The reverse flow will then transfer the target cells to the fluid port 31, 33 or to the connected fluid reservoir 3. In an embodiment, a pipette or similar tool may then be used to pipette up the fluid containing the target cells from the fluid port 31, 33 or fluid reservoir 3. The fluid containing the target cells is then injected into a fluid port 131, 133 of the flow input channel 130 of the downstream microfluidic device 100, or to a fluid reservoir that is connected to an end 132, 134 of this flow input channel 130.

A further alternative is to connect the fluid reservoir 3 that initially was connected to an end 32, 34 of the flow input channel 30 in the upstream microfluidic device 1 to an end 132, 134 of the flow input channel 130 of the downstream microfluidic device 100 once the reverse flow applied in step S6 has transferred the target cells from the cell channels 20 into the fluid reservoir 3. A flow controller 200 could then pump or otherwise transfer the fluid from the fluid reservoir 3 into the flow input channel 130 of the downstream microfluidic device 100.

The usage of multiple microfluidic devices 1, 100 in the cell capture thereby enriches the target cells and provides an efficient solution to obtain sufficient number of target cells for the subsequent characterization, even if the original biological sample contained very few target cells and/or a lot of contaminating particles.

The reduction of the flow in step S4 can be performed according to various embodiments. For instance, the flow of the biological sample in the flow channel 30, 60 could be interrupted, thereby stopped. In such an embodiment, there is typically no flow of the biological sample in the flow channel 30, 60. The reduction in step S4 is thereby a reduction to zero flow of the biological sample, i.e., a fully reduction of the flow.

In other embodiments, the flow of the biological sample in the flow channel 30, 60 does not need to be interrupted or stopped in step S4. In these embodiments, there is still a flow of the biological sample in the flow channel 30, 60. However, this flow is reduced as compared to the initial flow induced and established in the flow channel 30, 60 in step S1. The flow reduction could, for instance, be performed by reducing the flow velocity of the biological sample so that the flow velocity is X % of the initial flow velocity following step S1. This parameter X could be any value less than a 100, such as equal to or less than 95, equal to or less than 90, equal to or less than 85, equal to or less than 80, equal to or less than 75, equal to or less than 70, equal to or less than 65, equal to or less than 60, equal to or less than 55, equal to or less than 50, equal to or less than 45, equal to or less than 40, equal to or less than 35, equal to or less than 30, equal to or less than 25, equal to or less than 20, equal to or less than 15, equal to or less than 10, or equal to or less than 5.

A reduction of the flow in step S4 may in some applications, be preferred over fully interrupting the flow. Having a low flow in the flow channel 30, 60 reduces the risk of clogging, bubble formation, etc., in particular if the flow of the biological sample is once more resumed in the flow channel 30, 60 after the step S6.

In an embodiment, step S1 of FIG. 8 comprises inducing the flow of the biological sample in the flow input channel 30 of the upstream microfluidic device 1 between the first end 32 and the second end 34 of the flow input channel 30.

This embodiment is in particular suitable for an upstream microfluidic device 1 as shown in FIG. 1. Thus, in such a case, the flow of the biological sample is induced and established in the flow input channel 30. As the biological sample is flowing in the flow input channel 30, the sample will also flow through the cell channels 20 into the flow output channel 40 and out through the fluid port 41.

The cell channels 20 are adapted to accommodate the target cells. This means that the cell channels 20 have a size, such as diameter, width and height, and shape, to allow the target cells to enter the cell channels 20 through the respective first ends 22. Contaminating particles having a size, shape and/or rigidity that is too big or not adapted to the cross-sectional size and shape of the cell channels 20 will not enter the cell channels 20 but rather remain in the flow of the biological sample in the flow input channel 30.

The cell channels 20 comprise a respective obstruction 25 designed to prevent the target cells, such as of a particular size, dimension, shape, form or rigidity, from passing the respective obstruction 25 and into the flow output channel 40. The respective obstruction 25 is preferably arranged at or close to the second ends 24 of the cell channels 20.

In particular embodiments, the dimension of the cell channels 20 is in the range of 100 nm to 100 µm.

There is, thus, a separation between target cells and contaminating particles in the upstream microfluidic device 1. Large contaminating particles, contaminating particles having a cross-sectional shape that does not match the cell channels 20 and contaminating particles that are too rigid to be deformed to enter the first ends 22 of the cell channels 20 cannot enter the cell channels 20 and will thereby remain in the biological sample in the flow input channel 30. Correspondingly, small contaminating particles and contaminating particles that are easily deformed may enter the cell channels 20 but will also pass the obstruction 25 and flow into the flow output channel 40 and out through the fluid port 41. This means that the upstream microfluidic device 1 will mainly capture target cells in the cell channels 20 or at least lead to an enrichment of target cells in the cell channels 20. This means that the percentage of captured "particles" in the cell channels 20 that are target cells will be significantly higher as compared to the number of "particles" in the biological sample that are target cells.

The substrate 10 of the microfluidic device 1 has multiple, i.e., at least two but most generally several tens of, several hundred, or even several thousand or several hundred thousand, cell channels 20 extending between the flow input channel 30 and the flow output channel 40. The cell channels 20 are preferably parallel with each other as shown in FIG. 1 with the first ends 22 in fluid connection with the flow input channel 30 and the opposite second ends 24 in fluid connection with the flow output channel 40. Accordingly, a biological sample present in the flow input channel 30 may flow through the cell channels 20 and further into the flow output channel 40 and out through the fluid port 41. This high number of cell channels 20 provides several opportunities for target cells present in the biological sample in the flow input channel 30 to be captured in a cell channel 20.

Figure 2:
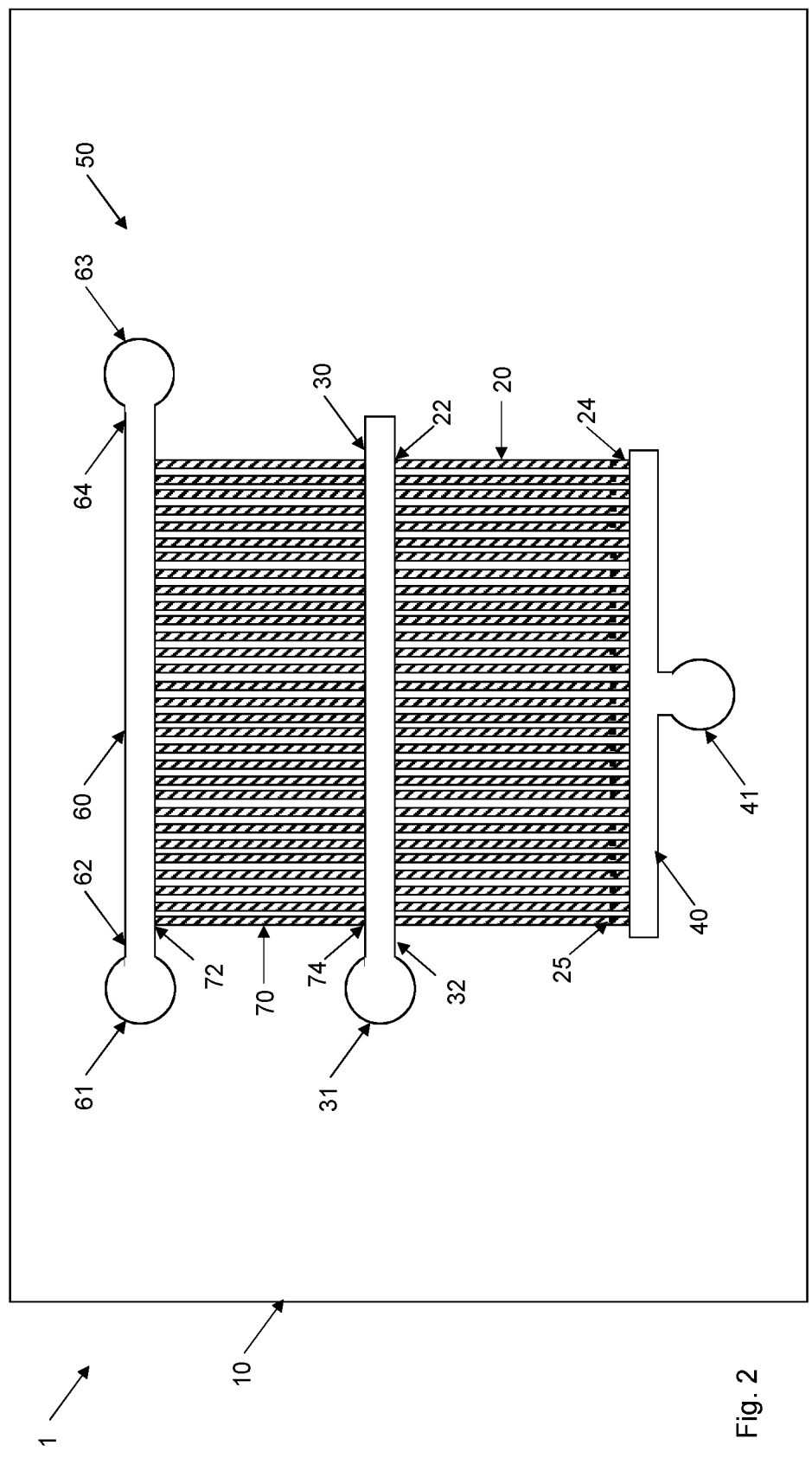
FIG. 2 is a schematic illustration of an upstream microfluidic device with a pre-filter according to an embodiment.

The upstream microfluidic device 1 may comprise a pre-filter 50 as shown in FIG. 2 to remove at least a portion of the contaminating particles, thereby preventing or at least significantly reducing the number of such contaminating particles that may reach the cell channels 20 used to capture target cells in the upstream microfluidic device 1. A significant advantage of the upstream microfluidic device 1 shown in FIG. 2 and the pre-filter 50 is that the pre-filter 50 can be cleaned if it would be clogged or obstructed by contaminating particles. Accordingly, even if the biological sample comprises a lot of such contaminating particles that may clog the pre-filter 50 and the upstream microfluidic device 1, the pre-filter 50 can be cleaned to remove such clogging contaminating particles to thereby continue capturing target cells from the biological sample in the upstream microfluidic device 1.

FIG. 2 is an illustration of an upstream microfluidic device 1 comprising a pre-filter 50. The pre-filter 50 comprises a filter channel 60 having a first end 62 and a second end 64. The pre-filter 50 also comprises pre-filter channels 70 adapted to accommodate the target cells. A respective first end 72 of the pre-filter channels 70 is in fluid connection with the filter channel 60 and a respective second end 74 of the pre-filter channels 70 is in fluid connection with the flow input channel 30.

In this embodiment, step S1 of FIG. 8 comprises inducing the flow of the biological sample in the filter channel 60 of the upstream microfluidic device 1 between the first end 62 and the second end 64 of the flow input channel 60.

In order to prevent or at least significantly reduce the risk of contaminating particles blocking the entrances, i.e., the first ends 22, of the cell channels 20 and thereby preventing any target cells in the biological sample from entering the cell channels 20 and become captured therein, the pre-filter 50 is arranged upstream of the cell channels 20. This means that the pre-filter 50 will effectively remove at least a significant portion of any contaminating particles present in the biological sample and thereby prevent or reduce the number of such contaminating particles from reaching the flow input channel 30 and the cell channels 20.

In the embodiment of the pre-filter 50 shown in FIG. 2, the pre-filter 50 comprises multiple pre-filter channels 70 that are preferably parallel to each other. These pre-filter channels 70 may, in an embodiment, be substantially similar to the cell channels 20 but with the exception of not having any obstruction 25 as the cell channels 20 have.

The pre-filter channels 70 may then have a same cross-sectional size and shape as the cell channel 20 or may have a different such cross-sectional size and/or shape as long as the target cells can enter and flow through the pre-filter channels 70.

The pre-filter channels 70 may have a substantially uniform cross-sectional size and shape when traveling from the first end 72 at the filter channel 60 towards the second end 74 at the flow input channel 30. In another embodiment, the cross-sectional size and/or shape may change, either continuously or in one or more steps, from the first end 72 to the second end 74. For instance, the diameter, width or height of the filter channels 70 could be larger at the first end 72 as compared to the second end 74. This narrowing of the pre-filter channels 70 could be continuous, i.e., smoothly decreasing diameter, width or height when going from the first end 72 to the second end 74. Alternatively, the narrowing of the pre-filter channels 70 could be step-wise in one or more steps.

The embodiment of having parallel pre-filter channels 70 interposed between substrate material should merely be seen as an illustrative example of a pre-filter 50. For instance, multiple pillars may be arranged in the pre-filter between the filter channel and the flow input channel. These multiple pillars form pre-filter channels extending between the pillars and from the filter channel to the flow input channel. In an embodiment, the pillars are uniformly distributed in a so-called pre-filter area or zone between the filter channel and the flow input channel. In such an embodiment, the inter-pillar distance between adjacent pillars is substantially the same throughout the pre-filter area or zone. In an alternative embodiment, the pillars may be more or less randomly distributed over the pre-filter area or zone as long as there are pre-filter channels extending between the filter channel and the input channel and having dimension sufficient to allow target cells to flow from the filter channel through the pre-filter area or zone and into the flow input channel.

In a further embodiment, the inter-pillar distance may change over the pre-filter area or zone, either continuously or step-wise, when going from the filter channel to the flow input channel. For instance, the inter-pillar distance could be smaller between adjacent pillars close to the flow input channel as compared to between adjacent pillars close to the filter channel.

In another embodiment, the pre-filter area or zone comprises a row or array of filter structures having openings in between. These openings thereby allow the target cells to pass through the row or array of filter structures.

A single row or array of filter structures may be arranged in the pre-filter area or zone. This should merely be seen as an illustrative example. It is in fact possible to have multiple such rows or arrays arranged one after another to basically form a matrix of filter structures. In such a case, the filter structures in different rows may be aligned to each other or may be at least partly displaced relative to each other. In the former case, the pre-filter channels would be straight channels between the openings in the filter structures, whereas in the latter case the pre-filter channels would zig-zag between displaced openings in different rows of filter structures.

In the case of multiple rows or arrays of filter structures, the distances between adjacent filter structures could be the same in all rows or arrays, i.e., having uniformed openings. Alternatively, the distances between adjacent filter structures could differ between different rows, such as having larger such distances and thereby openings for a row of filter structures close to the filter channel as compared to the distances and thereby openings for a row of filter structures close to the flow input channel.

There are further alternative ways of forming pre-filter channels 70 in a pre-filter area or zone than having parallel pre-filter channels 70 as in FIG. 2, pillar-defining pre-filter channels and pre-filter channels between filter structures. The embodiments are thereby not limited to these illustrative examples. For instance, continuous pores extending through the substrate or a semi-permeable membrane structure arranged in the pre-filter area or zone between the filter channel and the flow input channel could alternative be used as pre-filter channels.

In operation, a flow of the biological sample is induced in step S1 in the filter channel 60 between the respective ends 62, 64. The biological sample will also flow into the pre-filter channels 70. Contaminating particles present in the biological sample and having a sufficiently large size, shape and/or rigidity are prevented from entering the first ends 72 of the pre-filter channels 70 and thereby remain in the filter channel 60. However, any target cells present in the biological sample will enter the first ends 72 and flow through the pre-filter channels 70 into the flow input channel 30. If the pre-filter channels 70 have changing size and/or dimension, contaminating particles may actually enter the pre-filter channels 70 through the first ends 72 but may then become stuck somewhere along the length of the pre-filter channels 70 due to being too large or having a shape preventing them from flowing further through the pre-filter area or zone 75 towards the second ends 74 of the pre-filter channels 70.

The flow of biological sample continues from the flow input channel 30 through the cell channels 20 and then out into the flow output channel 40 and the fluid port 41. Any target cells present in the flow of biological sample will be trapped in the cell channels 20 due to the presence of the obstructions 25.

If the pre-filter 50 needs to be cleaned due to contaminating particles clogging the pre-filter channels 70 and/or blocking the entrances of the pre-filter channels 70, a reverse fluid flow can be established from a fluid port 31 of the flow input channel 30 and out through a filter port 61, 63 of the filter channel 60. The fluid will then flow from the flow input channel 30 and through the pre-filter channels 70 but in the reverse direction, i.e., from the second end 74 towards the first end 72, and then into the filter channel 60. Clogging contaminating particles will then be washed away by the reverse fluid flow and flow out through the filter port 61, 63.

This reverse flow is preferably a flow of a fluid lacking any contaminating particles, such as a culture medium, a wash medium or other liquid.

During the cleaning of the pre-filter 50, by having a flow from the fluid port 31 of the flow input channel 30, the fluid preferably also flows into the cell channels 20, through the flow output channel 40 and out through the fluid port 41. This flow through the cell channels 20 during the cleaning of the pre-filter 50 reduces the risk of washing away any target cells captured in the cell channels 20. Accordingly, any target cells already captured in cell channels 20 will be retained during the cleaning process.

Figure 3:
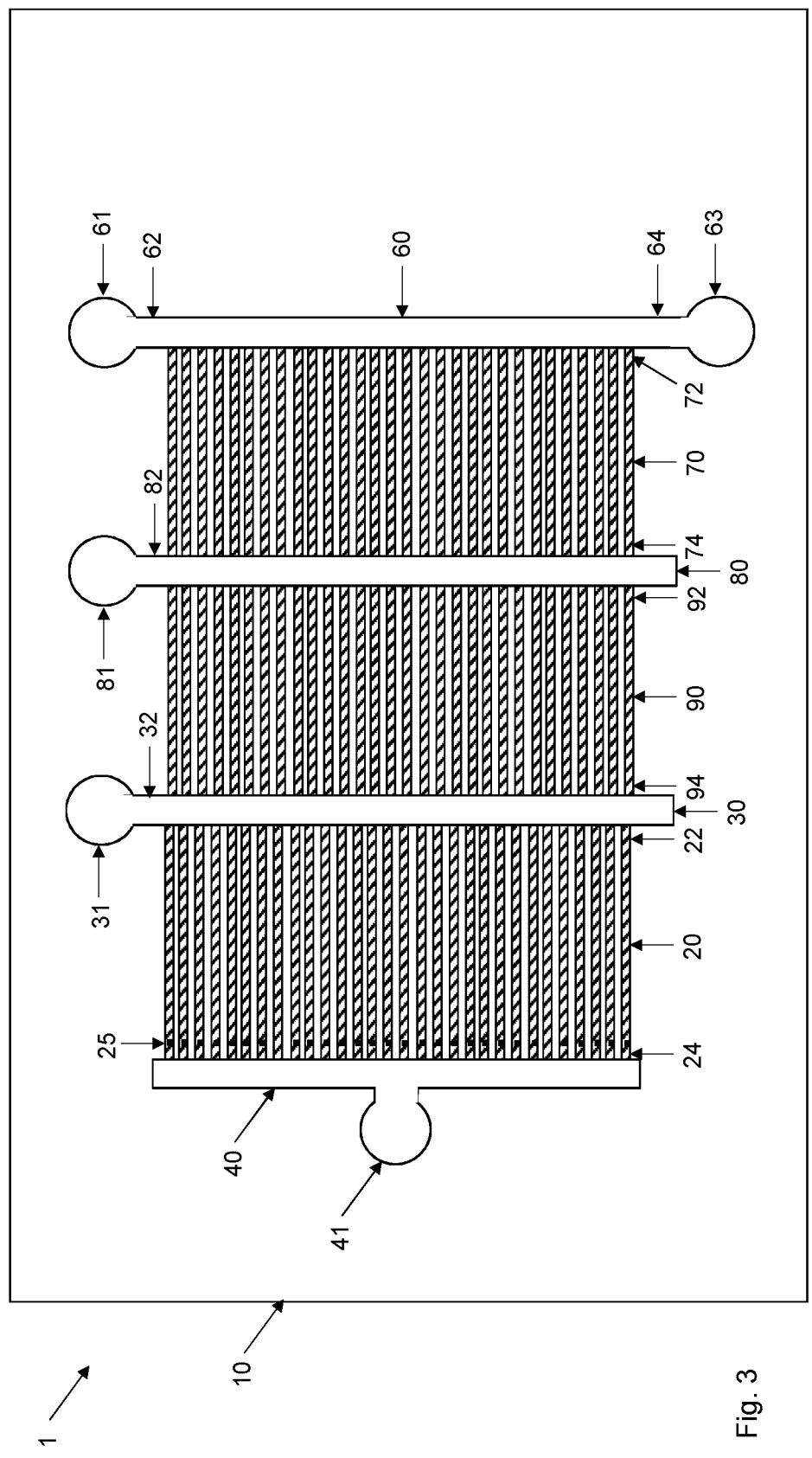
FIG. 3 is a schematic illustration of an upstream microfluidic device with a pre-filter according to another embodiment.

FIG. 3 is an illustration of another embodiment of an upstream microfluidic device 1 having multiple sets of pre-filter channels 70, 90. In this embodiment, the filter channel 60 is an upstream filter channel 60 and the pre-filter channels 70 are upstream pre-filter channels 70. The pre-filter 50 also comprises a downstream filter channel 80 and downstream pre-filter channels 90 adapted to accommodate the target cells. A respective first end 92 of the downstream pre-filter channels 90 is in fluid connection with the downstream filter channel 80 and a respective second end 94 of the downstream pre-filter channels 90 is in fluid connection with the flow input channel 30. In this embodiment, the respective first end 72 of the upstream pre-filter channels 70 is in fluid connection with the upstream filter channel 60 and the respective second end 74 of the upstream pre-filter channels 70 is in fluid connection with the downstream filter channel 80.

In this embodiment, step S1 of FIG. 8 preferably comprises inducing the flow of the biological sample in the upstream filter channel 60 between the first end 62 and the second end 64 of the upstream filter channel 60.

Thus, the embodiment as illustrated in FIG. 3 comprises a pre-filter 50 with multiple, i.e., at least two, sets of filter channels 60, 80 and pre-filter channels 70, 90. These sets are then arranged in series in the substrate 10 with an upstream set of the upstream filter channel 60 and the upstream pre-filter channels 70 and a downstream set of the downstream filter channel 80 and the downstream pre-filter channels 90 and where upstream vs. downstream relates to a flow direction from the upstream filter channel 60 towards the flow output channel 40.

In an embodiment, the downstream pre-filter channels 90 and the upstream pre-filter channels 70 have the same diameter, width and height and the same cross-sectional shape. This means that the two sets of filter channels 60, 80 and pre-filter channels 70, 90 are substantially the same. In another embodiment, the downstream pre-filter channels 90 may have a different diameter, width and height and/or cross-sectional shape as compared to the upstream pre-filter channels 70. In particular, the upstream pre-filter channels 70 have a larger diameter or a larger height and/or width as compared to the downstream pre-filter channels 90.

Accordingly, the cross-sectional area of the pre-filter channels 70, 90 is preferable larger for the upstream pre-filter channels 70 as compared to the downstream pre-filter channels 90. If at least one of the upstream and downstream pre-filter channels 70, 90 have narrowing cross-sectional shape then the diameter, width and/or height of the upstream pre-filter channels 70 at the second end 74 is preferably larger than the diameter, width and/or height of the downstream pre-filter channels 90 at the second end 94.

Both the upstream and downstream pre-filter channels 70, 90 could have uniform cross-sectional shape and size when traveling from the first end 72, 92 to the second end 74, 94. Alternatively, one or both of the upstream and downstream pre-filter channels 70, 90 could have different cross-sectional shape and 30 size at the first end 72, 92 as compared to the second end 74, 94, such as continuously or step-wise narrowing pre-filter channels 70, 90.

This concept of having multiple filter channels 60, 80 and multiple pre-filter channels 70, 90 can of course be extended to more than two sets of such filter channels 60, 80 and pre-filter channels 70, 90, possibly with different dimensions.

The pre-filter 50 shown in FIG. 3 can be cleaned from clogging contaminating particles according to various embodiments. For instance, each set of pre-filter channels 70, 90 can be individually cleaned. A separate cleaning of the upstream pre-filter channels 70 can be performed by directing a reverse flow from a filter port 81 in fluid connection to an end of the downstream filter channel 80 through the downstream filter channel 80 and the upstream pre-filter channels 70 and the upstream filter channel 60 and out though a filter port 61, 63 of the upstream filter channel 60. Correspondingly, a separate cleaning of the downstream pre-filter channels 90 may be performed by directing a reverse flow from a fluid port 31 of the flow input channel 30 through the flow input channel 30 and the downstream pre-filter channels 90 and the downstream filter channel 80 and out through the filter port 81 of the downstream filter channel 80.

Alternatively, the two sets of pre-filter channels 70, 90 can be cleaned in a combined operation by providing a reverse flow from the fluid port 31 of the flow input channel 30, the flow input channel 30 and through the downstream pre-filter channels 90, the downstream filter channel 80, the upstream pre-filter channels 70 and the upstream filter channel 60 and out through any or all of its connected filter ports 61, 63.

The flow channel in which the flow of the biological sample is induced in step S1 can either be the flow input channel 30 for an upstream microfluidic device 1 lacking any pre-filter 50 as shown in FIG. 1 or the (upstream) filter channel 60 for an upstream microfluidic device 1 comprising a pre-filter 50 as shown in FIGS. 2 and 3.

In either case, in an embodiment, step S1 of FIG. 8 comprises inducing an oscillating flow of the biological sample back and forth between the first end 32, 62 and the second end 34, 64 of the flow channel 30, 60.

In a particular implementation of this embodiment, a first fluid reservoir 2 is connected to a first fluid port 31 in fluid connection with the first end 32 of the flow input channel 30 or to a first filter port 61 in fluid connection with the first end 62 of the (upstream) filter channel 60. A second fluid reservoir 4 is preferably connected to a second fluid port 33 in fluid connection with the second end 34 of the flow input channel 30 or to a second filter port 63 in fluid connection with the second end 64 of the (upstream) filter channel 60. In such a case, a flow controller 200 could be configured to induce a flow of the biological sample from the first fluid reservoir 2 through the first (fluid or filter) port 31, 61, through the filter channel (flow input channel 30 or (upstream) filter channel 60) and out through the second (fluid or filter) port 33, 63 and into the second fluid reservoir 4. The flow controller 200 is then configured to induce a flow of the biological sample in the opposite direction, i.e., from the second fluid reservoir 4 through the second (fluid or filter) port 33, 63, through the flow channel (flow input channel 30 or (upstream) filter channel 60) and out through the first (fluid or filter) port 31, 61 and into the first fluid reservoir 2.

In another embodiment, step S1 of FIG. 8 comprises inducing a circular flow of the biological sample between the first end 32, 62 and the second end 34, 64 of the flow channel 30, 60 and through a fluid connector 35, see FIG. 4, interconnecting the first end 32, 62 and the second end 34, 64 of the flow channel 30, 60.

In this embodiment, the flow controller 200 is configured to induce a circular flow of the biological sample, such as between the first fluid or filter port 31, 61 and the second fluid or filter port 33, 63. The biological sample then flows in one and the same direction rather than oscillating back and forth. In such a case, there is a fluid connection between the first fluid or filter port 31, 61 and the second fluid or filter port 33, 63 as schematically illustrated in FIG. 4. This fluid connector 35 preferably comprises at least one fluid reservoir (not illustrated) adapted to contain the biological sample. The fluid connector 35 could be any connection in which the biological sample can flow, such as a tubing or a channel in the substrate 10.

In either case, the biological sample can flow in the flow channel 30, 60 to thereby increase the chances of capturing any target cells present therein in the cell channels 20. In addition, the flow of the biological sample in the flow channel 30, 60 by the control of the flow controller 200 allows a culturing of the target cells in the biological sample. This means that even if the biological sample initially comprises very few target cells, the culturing allows these target cells to grow and multiply during the oscillating or circular flow of the biological sample. Accordingly, the chances of capturing target cells in the cell channels 20 will thereby increase over time.

It is possible to switch between an oscillating flow and a circular flow if the upstream microfluidic device 1 comprises or is connectable to suitable fluid reservoirs 2, 4 and fluid connector 35.

In an embodiment, the flow controller 200 is a pressure controller providing a pressure-driven flow. In such a case, the pressure controller is configured to control a fluid pressure applied to the fluid ports 31, 33, 41 and the filter ports 61, 63 to control the direction of the fluid flow.

A non-limiting, but illustrative, example of such a pressure controller that can be used is proportional pressure regulator VEAB by Festo AG.

Other flow control solutions could include using one or more pumps in connection with valves in order to control the direction of fluid flow.

The monitoring of the cell channels 20 in step S2 could include taking at least one image of the cell channels 20. A single image at a single time instance could be taken or multiple images at multiple time instances are taken.

In a particular embodiment, the at least one image is taken using a microscopy, such as a phase contrast microscope, connected to a camera, such as charge-coupled device (CCD) camera or a complementary metal-oxide semiconductor (CMOS) camera, or a confocal scanning system for fluorescence, Raman imaging, Coherent Anti-stokes Raman Scattering (CARS), Stimulated Raman Scattering (SRS) and similar chemically sensitive techniques that gives spectral changes for dead and live cells. This includes measurements in one or several wavelengths with or without contrast enhancing additions to the growth media, such as chemically specific probes and dyes.

An image is not necessarily a 2D photo of an area but can also correspond to, for example, line scans in selected positions in the upstream microfluidic device 1.

Other techniques of detecting presence of target cells in cell channels 20 could be used instead of or as a complement to taking images of the cell channels 20, such as measuring conductivity through the cell channels 20 or the heat production in the cell channels 20 using electronic measurement equipment.

Figure 9:
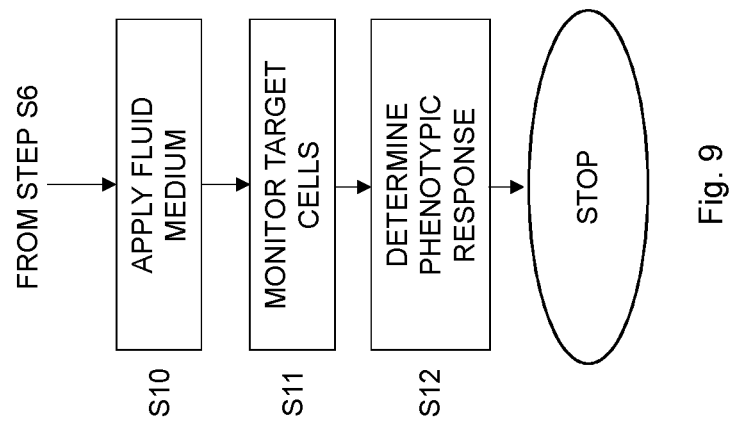
FIG. 9 is a flow chart illustrating additional, optional steps of the method shown in FIG. 8.

Once the target cells captured in the upstream microfluidic device 1 have been transferred to the downstream microfluidic device 100 by applying a reverse fluid flow in step S6 of FIG. 8, the target cells captured in the cell channels 120 of the downstream microfluidic device 100 can be characterized. An embodiment of such a cell characterization is shown in FIG. 9.

The method continues from step S6 in FIG. 8. A next step S10 comprises applying a fluid medium comprising or constituting a test agent at the first end 132 and/or the second end 134 of the flow input channel 130 in the downstream microfluidic device 100. The next step S11 comprises monitoring target cells in the cell channels 120. A phenotypic response of the target cells to the test agent is determined in step S12 based on the monitoring of target cells in the cell channels 120.

Thus, the downstream microfluidic device 100 is useful for monitoring or analyzing phenotypic characteristics of target cells present in a biological sample, such as a phenotypic response of the target cells to a test agent.

The test agent could be any molecule, compound, composition, or a mixture of molecules, compounds or compositions. In related embodiments, the target cells are more generally exposed to one or more stimuli in the cell channels 120. Such one or more stimuli do not necessarily have to be a test agent but could instead be a change in environmental conditions, such as temperature change. Thus, the phenotype response of the target cells to the one or more stimuli is then determined.

Determining the phenotypic response of the target cells to the test agent in step S12 could include determining at least one of growth rate, shape, size, form of growth rate curve defining growth rate over time, form of length curve defining cell length over time, form of area curve defining cell area over time, color, optical density, absorption spectra, conductivity, heat production or a mixture thereof for the target cells.

The determination of the phenotypic response of the target cells in step S12 is preferably performed based on monitoring, in step S11, the target cells in the cell channels 120, once or at multiple time instances. Thus, depending on the particular phenotypic response of the target cells to the test agent it might be sufficient to monitor the target cells once or at multiple time instances in step S11.

The monitoring of the target cells in step S11 could include taking at least one image of the target cells in the cell channels 120. A single image at a single time instance could be taken or multiple images at multiple time instances are taken.

In a first implementation example, the test agent is an antibiotic. In this implementation example, a susceptibility of target cells, such as bacteria, to the antibiotic can be determined in step S12 based on the monitoring of target cells in the cell channels 120.

In a second implementation example, the test agent is a cytostatic. In such an implementation example, a susceptibility of the target cells, such as cancer cells, to the cytostatic can be determined in step S12 based on the monitoring of target cells in the cell channels 120.

In a third implementation example, the test agent is a probe, such as a fluorescent in situ hybridization (FISH) probe. In such a case, the FISH probe can be used to identify the particular target cells captured in the cell channels 120 based on the monitoring of the target cells in the cell channels 120. Different such FISH probes target different target cells, thereby enabling determination of the identity of the target cells depending on whether the FISH probe binds specifically to the target cell or not. The FISH probes can target species-specific RNA or DNA sequences, such as 23S rRNA. For more information of using FISH probes for identifying microorganisms in blood culture reference is made to Kempf et al., Journal of *Clinical Microbiology* 2000, 38(2): 830-838. FISH probes adapted for different bacteria can be found on http://probebase.csb.univie.ac.at/node1/8.

The identification of species can advantageously be combined with determining the phenotypic response of the target cells against a test agent according to any of the above presented implementation examples. In such a case, the species identification is preferably done after the phenotypic response to antibiotics or cytostatics. In this way, the species identification may facilitate the interpretation of the phenotypic response to the test agent in the cell channels 120, which is particularly advantageous if the biological sample comprises a mixture of target cells of species or strains.

In an embodiment, the biological sample is a blood sample, such as a whole blood sample, a diluted blood sample or a blood culture sample. Other examples of biological samples include other body fluid samples, such as a urine sample, a saliva sample, a feces sample, a cerebrospinal fluid sample, an amniotic fluid sample, a milk sample, a sputum derived sample or a lymph sample. Alternatively, the biological sample could be obtained from a body tissue, such as a biopsy. Other examples include food sample tested for bacterial contaminations, milk from cow, goats or other milk producing animals for mastitis testing, etc. Actually, any biological sample that comprises cells and that can be loaded into a microfluidic device can be used according to the embodiments.

Figure 5:
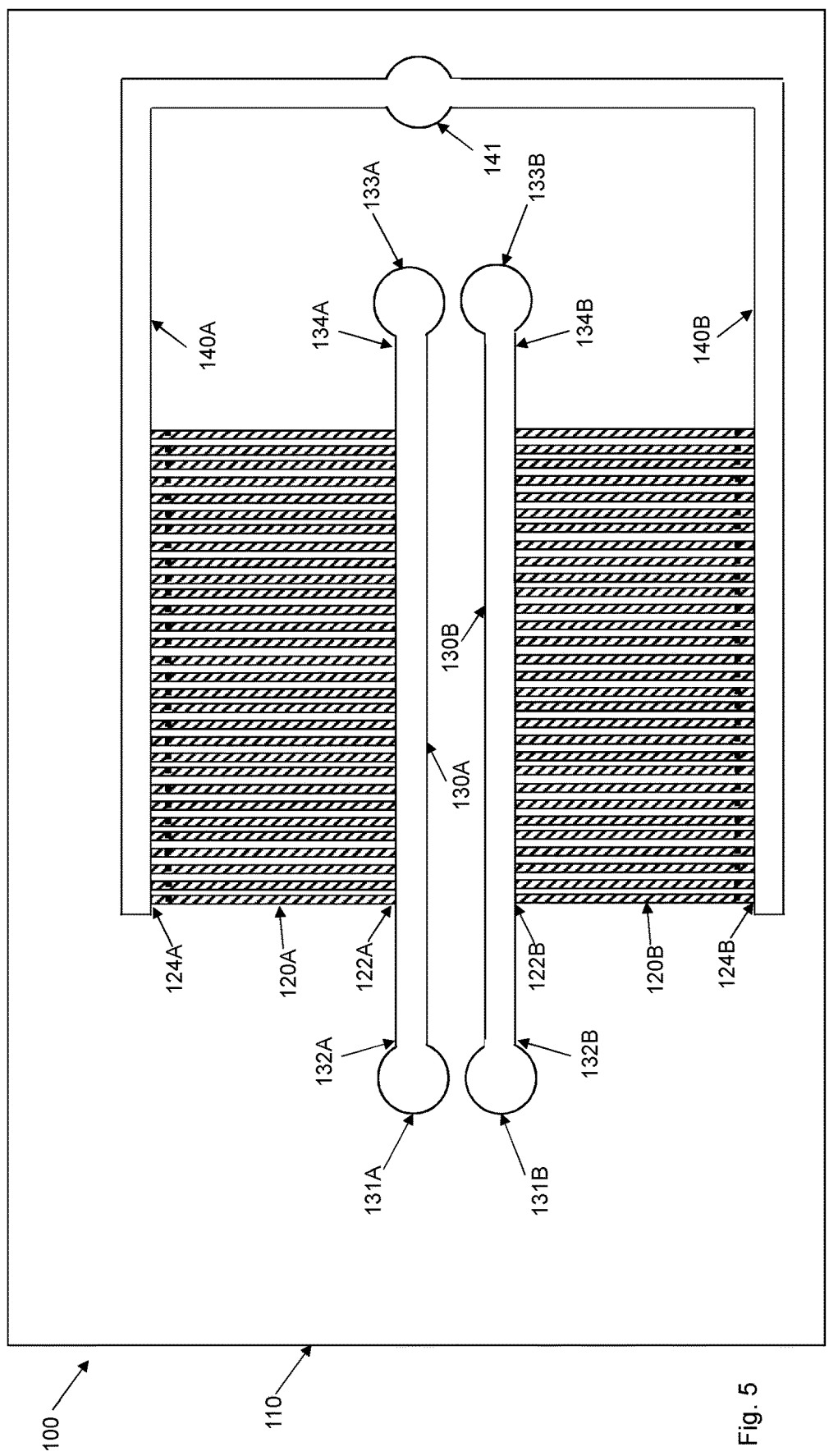
FIG. 5 is a schematic illustration of a downstream microfluidic device according to an embodiment.
Figure 6:
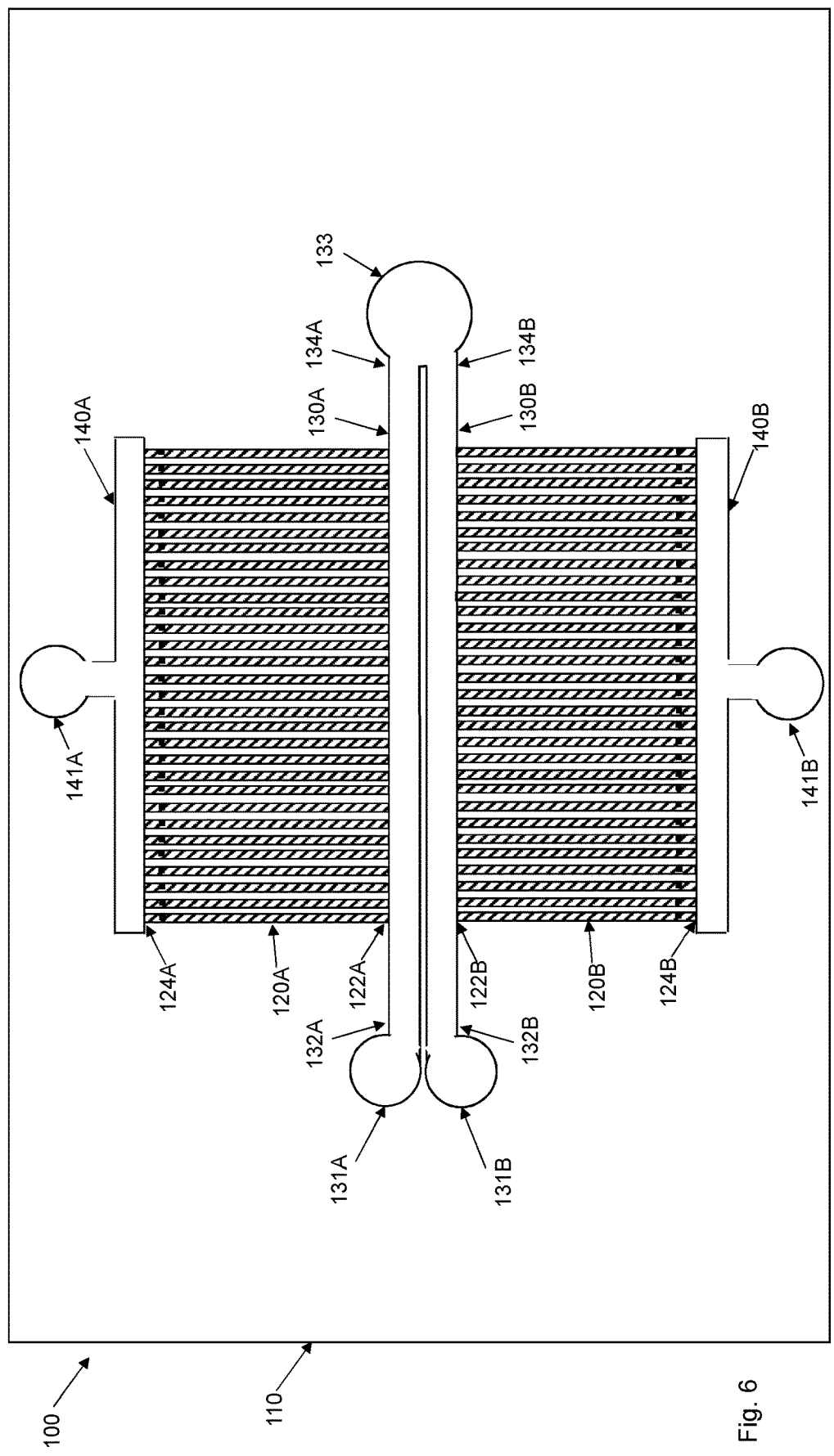
FIG. 6 is a schematic illustration of a downstream microfluidic device according to another embodiment.

FIGS. 5 and 6 illustrate a downstream microfluidic device 100 with a substrate 110 having multiple, such as two, sets of cell channels 120A, 120B adapted to accommodate the target cells. Each set of the multiple sets has a respective flow input channel 130A, 130B having a respective first end 132A, 132B in fluid connection with a respective first fluid port 131A, 131B and a respective second end 134A, 134B in fluid connection with a respective second fluid port 133A, 133B or a common second fluid port 133. Each set of the multiple sets has a respective flow output channel 140A, 140B in fluid connection with a respective third fluid port 141A, 141B or a common third fluid port 141.

Such a downstream microfluidic device 100 can be used to test the phenotypic response of captured target cells to a test agent in one set of fluid channels 120A, while another set of fluid channels 120B is used as a control, i.e., any target cells captured therein are not exposed to the test agent, or are exposed to another test agent.

In these embodiments, target cells captured in cell channels 120A of the first set are exposed to the test agent whereas target cells captured in the cell channels 120B of the second set are not exposed to the test agent.

An advantage of the embodiments of the downstream microfluidic device 100 as shown in FIGS. 5 and 6 is that it is possible to have an internal control by having multiple sets of cell channels 120A, 120B in the same substrate 110.

The various embodiments shown in FIGS. 5 to 6 may be combined and modified. For instance, a common second fluid port 133 as shown in FIG. 6 could be used together with a common third fluid port 141 as shown in FIG. 5. Furthermore, usage of respective third fluid ports 141A, 141B as shown in FIG. 6 could be used in the downstream microfluidic device 100 of FIG. 5.

FIG. 4 illustrates the upstream microfluidic device 1 together with the downstream microfluidic device 100. The figure also schematically indicates a switchable fluid connector 6 that either connects one of the ends 34 of the flow input channel 30 of the upstream microfluidic device 1 with one of the ends 132 of the flow input channel 130 of the downstream microfluidic device 100 or a fluid connector 35 as shown in FIG. 4 or a fluid reservoir 4 as shown in FIG. 7.

The upstream microfluidic device 1 could be according to any of the embodiments disclosed herein, such as illustrated in FIGS. 1-3. Correspondingly, the downstream microfluidic device 100 could be according to any of the embodiments disclosed herein, such as illustrated in FIGS. 1, 5, 6.

The two microfluidic devices 1, 100 could include a respective separate substrate 10, 110. Alternatively, the two microfluidic devices 1, 100 could be provided in one and the same substrate that then includes all the channels 20, 30, 40, 120, 130, 140 of both the upstream and downstream microfluidic devices 1, 100. The fluid ports 31, 33, 41, 131, 131, 133, 141 (and filter ports 61, 63, 81 if the upstream microfluidic device 1 comprises a pre-filter 50) could be provided in the substrate(s) 10, 110 or be arranged outside of the substrate(s) 10, 110 and then in fluid connection with the channels 30, 40, 130, 140 using respective fluid connections, such as tubing.

The substrate(s) 10, 110 of the upstream and downstream microfluidic device 1, 100 may be made of any material, such as plastic material, in which the structures constituting the cell channels 20, 120, the flow input channel 30, 130, the flow output channel 40, 140 and optionally the pre-filter 50 can be defined.

Non-limiting examples of suitable materials for the substrate(s) 10, 110 include ZEONEX® and ZEONOR®, which are cyclic olefin polymers (COP) marketed by ZEON Chemicals L. P. and TOPAS®, which are cyclic olefin copolymers (COC) marketed by Topas Advanced Polymers. These materials have excellent optical characteristics in terms of transmission and background fluorescence. They also have good flow characteristics when heated and may therefore replicate small structures allowing formation of substrates of the microfluidic device.

Other examples of suitable materials for the substrate(s) 10, 110 include glasses, polydimethylsiloxane (PDMS), poly(methyl methacrylate) (PMMA), polycarbonate (PC), polypropylene (PP), polytetrafluoroethylene (PTFE), polyethylene terephthalate (PET) and poly(p-phenylene sulfide) (PPS).

The substrate 10, 110 is preferably transparent to allow imaging through the substrate 10, 110.

In an embodiment, a common lid or separate lids (not illustrated) are arranged onto the substrate(s) 10, 110. The lid(s) then function(s) as a cover or lid for the channels 20, 30, 40, 120, 130, 140 defined in the substrate(s) 10, 110. The lid(s) could be made of a plastic material or glass. The lid(s) is(are) preferably transparent to allow imaging through the lid(s).

FIG. 7 schematically illustrates a flow controller 200 connected to a microfluidic device 1. This flow controller 200 is preferably used to control the flows of both the upstream microfluidic device and the downstream microfluidic device. Alternatively, separate flow controllers 200 could be used for controlling the fluid flows in the two microfluidic devices. The flow controller 200 is preferably connected to all the fluid ports (and filter ports) of the microfluidic devices 1. The connection could be a direct connection between the flow controller 200 and the fluid ports (and filter ports) or via a respective fluid reservoirs 2, 3, 4, 5 as schematically illustrated in FIG. 7.

Another aspect of the embodiments relates to a system for capturing target cells from a biological sample. The system comprises an upstream microfluidic device 1, a downstream microfluidic device 100, a fluid connector 6 and a flow controller 200. The upstream microfluidic device 1 comprises a substrate 10 having cell channels 20 adapted to accommodate the target cells, a flow input channel 30 having a first end 32 and a second end 34 and a flow output channel 40 in fluid connection with a fluid port 41. A respective first end 22 of the cell channels 20 is in fluid connection with the flow input channel 30 and a respective second end 24 of the cell channels 20 is in fluid connection with the flow output channel 40. The cell channels 20 comprise a respective obstruction 25 designed to prevent the target cells from passing the respective obstruction 25 and into the flow output channel 40. The downstream microfluidic device 100 comprises a substrate 110 having cell channels 120 adapted to accommodate the target cells, a flow input channel 130 having a first end 132 and a second end 134 and a flow output channel 140 in fluid connection with a fluid port 141. A respective first end 122 of the cell channels 120 is in fluid connection with the flow input channel 130 and a respective second end 124 of the cell channels 120 is in fluid connection with the flow output channel 140. The cell channels 120 comprise a respective obstruction 125 designed to prevent the target cells from passing the respective obstruction 125 and into the flow output channel 140. The flow controller 200 is adapted to induce a flow of the biological sample comprising the target cells in a flow channel 30, 60 of the upstream microfluidic device 1 between a first end 32, 62 and a second end 34, 64 of the flow channel 30, 60.

The fluid connector 6 is adapted to interconnect, when at least a minimum number of target cells are captured in the cell channels 20 of the upstream microfluidic device 1, the first end 32 and/or the second end 34 of the flow input channel 30 of the upstream microfluidic device 1 to the first end 132 and/or the second end 134 of the flow input channel 130 of the downstream microfluidic device 100. The flow controller 200 is adapted to, when at least a minimum number of target cells are captured in the cell channels 20 of the upstream microfluidic device 1, reduce the flow of the biological sample in the flow channel 30, 60 and apply a fluid medium at the fluid port 41 of the upstream microfluidic device 1 to release the target cells captured in the cell channels 20 of the upstream microfluidic device 1 and transfer the target cells into the cell channels 120 of the downstream microfluidic device 100.

In an embodiment, the flow controller 200 is adapted to, when at least a minimum number of target cells are captured in the cell channels 20 of the upstream microfluidic device 1, interrupt the flow of the biological sample in the flow channel 30, 60.

In an embodiment, the flow controller 200 is adapted to induce the flow of the biological sample in the flow input channel 30 of the upstream microfluidic device 1 between the first end 32 and the second end 34 of the flow input channel 30.

In an embodiment, the upstream microfluidic device 1 comprises a pre-filter 50. The pre-filter 50 comprises a filter channel 60 having a first end 62 and a second end 64 and pre-filter channels 70 adapted to accommodate the target cells. A respective first end 72 of the pre-filter channels 70 is in fluid connection with the filter channel 60 and a respective second end 74 of the pre-filter channels 70 is in fluid connection with the flow input channel 30. In such an embodiment, the flow controller 200 is adapted to induce the flow of the biological sample in the filter channel 60 of the upstream microfluidic device 1 between the first end 62 and the second end 64 of the filter channel 60.

In an embodiment, the filter channel 60 is an upstream filter channel 60 and the pre-filter channels 70 are upstream pre-filter channels 70. The pre-filter 50 then also comprises a downstream filter channel 80 and downstream pre-filter channels 90 adapted to accommodate the target cells. A respective first end 72 of the upstream pre-filter channels 70 is in fluid connection with the upstream filter channel 60, a respective second end 74 of the upstream pre-filter channels 70 is in fluid connection with the downstream filter channels 80, a respective first end 92 of the downstream pre-filter channels 90 is in fluid connection with the downstream filter channels 80 and a respective second end 94 of the downstream pre-filter channels 90 is in fluid connection with the flow input channel 30. In this embodiment, the flow controller 200 is adapted to induce the flow of the biological sample in the upstream filter channel 60 of the upstream microfluidic device 1 between the first end 62 and the second end 64 of the upstream filter channel 60.

In an embodiment, the flow controller 200 is adapted to induce an oscillating flow of the biological sample back and forth between the first end 32, 62 and the second end 34, 64 of the flow channel 30, 60.

In an embodiment, the flow controller 200 is adapted to induce a circular flow of the biological sample between the first end 32, 62 and the second end 34, 64 of the flow channel 30, 60 and through a fluid connector 35 interconnecting the first end 32, 62 and the second end 34, 64 of the flow channel 30, 60.

In an embodiment, the system further comprises a microscopy-based imaging system adapted to take at least one image of the cell channels 20 in the upstream microfluidic device 100.

In an embodiment, the flow controller 200 is adapted to apply a fluid medium comprising or constituting a test agent at the first end 132 and/or the second end 134 of the flow input channel 130 in the downstream microfluidic device 100.

In an embodiment, the substrate 110 of the downstream microfluidic device 100 has multiple sets of cell channels 120A, 120B adapted to accommodate the target cells. Each set of the multiple sets has a respective flow input channel 130A, 130B having a respective first end 132A, 132B in fluid connection with a respective first fluid port 131A, 131B and a respective second end 134A, 134B in fluid connection with a respective second fluid port 133A, 133B or a common second fluid port 133. Each set of the multiple sets has a respective flow output channel 140A, 140B in fluid connection with a respective third fluid port 141A, 141B or a common third fluid port 141. In such an embodiment, the flow controller 200 is adapted to apply the fluid medium comprising or constituting the test agent in a first fluid port 131A of a first set of the multiple sets and applying a fluid medium lacking the test agent or comprising or constituting another test agent in a first fluid port 131B of a second set of the multiple sets.

Figure 10:
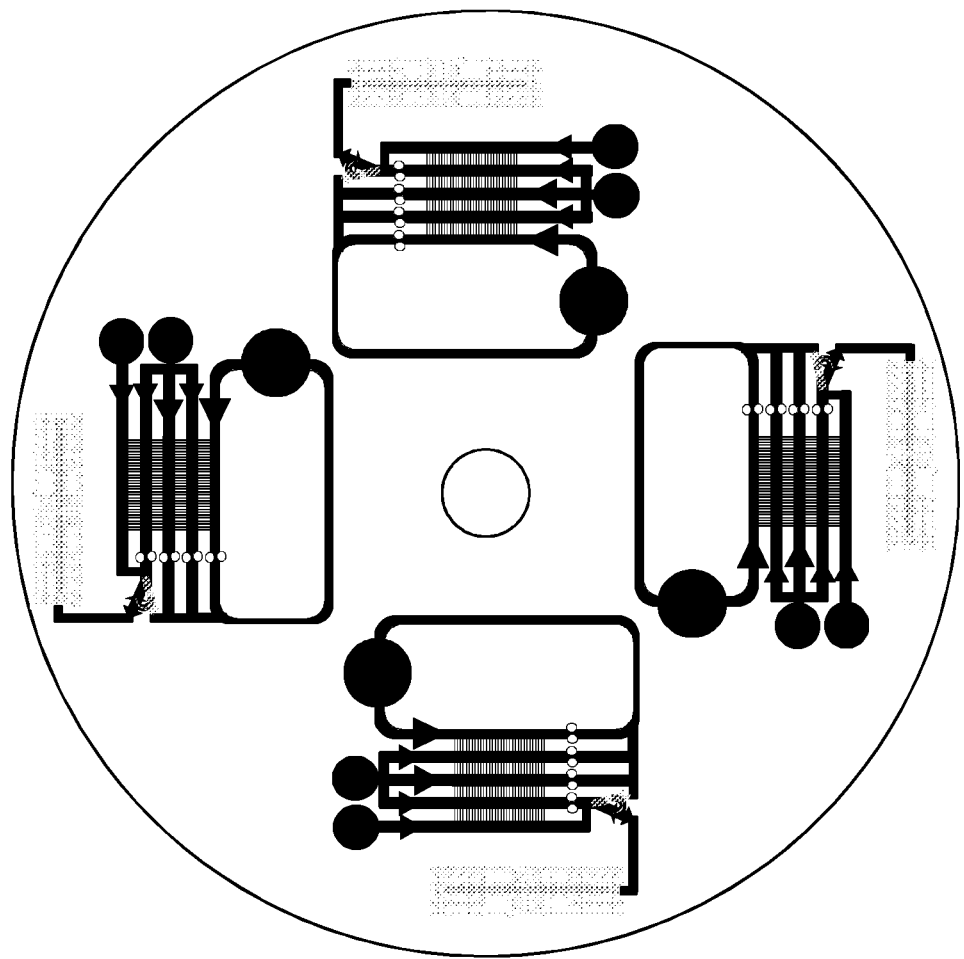
FIG. 10 illustrates arrangement of microfluidic devices on a disc according to an embodiment.

FIG. 10 schematically illustrates a disc comprising multiple systems of upstream and downstream microfluidic devices. Such an approach enables automatization and efficient analysis in parallel of multiple biological samples. For instance, one loading station or robot could be used to load biological samples at a given position. The disc is then turned to align a new system with this loading position. Correspondingly, a microscopy-based imaging system could be arranged at a given monitoring position to monitor target cells captured in cell channels. The disc can then be turned to align different systems with the imaging system once a monitoring session should be initiated.

The inclusion of multiple systems on, for instance, a disc additionally enables efficient usage of pumps and flow controllers, which may be shared by different systems.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of capturing target cells from a biological sample, said method comprising:
   providing an upstream microfluidic device comprising:
      a substrate having first cell channels adapted to accommodate said target cells;
      a first flow input channel having a first end and a second end; and
      a first flow output channel in fluid connection with a first output fluid port, wherein a respective first end of said first cell channels is in fluid connection with said first flow input channel, a respective second end of said first cell channels is in fluid connection with said first flow output channel, and said first cell channels comprise a respective obstruction designed to prevent said target cells from passing said respective obstruction and into said first flow output channel;
   inducing a flow of a biological sample comprising said target cells in a flow channel of the upstream microfluidic device between a first end and a second end of said flow channel,
   monitoring said first cell channels to detect a presence of target cells captured in said cell channels;
   when at least a minimum number of target cells are captured in said first cell channels:
      reducing said flow of said biological sample in said flow channel; and
      applying a fluid medium at said first output fluid port of said upstream microfluidic device to release said target cells captured in said first cell channels of said upstream microfluidic device and to enable transfer of said target cells into second cell channels of a downstream microfluidic device, said downstream microfluidic device comprising:
         a substrate having said second cell channels adapted to accommodate said target cells;
         a second flow input channel having a first end and a second end, wherein the second flow input channel is in fluid commination with the released target cells; and
         a second flow output channel in fluid connection with a second output fluid port, wherein a respective first end of said second cell channels is in fluid connection with said second flow input channel, a respective second end of said second cell channels is in fluid connection with said second flow output channel, and said second cell channels comprise a respective obstruction designed to prevent said target cells from passing said respective obstruction and into said second flow output channel.

2. The method according to claim 1, further comprising connecting said first end and/or said second end of said first flow input channel of said upstream microfluidic device to said first end and/or said second end of said second flow input channel of said downstream microfluidic device.

3. The method according to claim 1, wherein reducing said flow comprises interrupting said flow of said biological sample in said flow channel.

4. The method according to claim 1, wherein inducing said flow comprises inducing said flow of said biological sample in said first flow input channel of said upstream microfluidic device between said first end and said second end of said first flow input channel of said upstream microfluidic device.

5. The method according to claim 1, wherein said upstream microfluidic device comprises a pre-filter comprising:
- a filter channel having a first end and a second end; and
- pre-filter channels adapted to accommodate said target cells, wherein a respective first end of said pre-filter channels is in fluid connection with said filter channel and a respective second end of said pre-filter channels is in fluid connection with said first flow input channel of said upstream microfluidic device; and
- inducing said flow comprises inducing said flow of said biological sample in said filter channel of said upstream microfluidic device between said first end and said second end of said filter channel.

6. The method according to claim 5, wherein said filter channel is an upstream filter channel;
said pre-filter channels are upstream pre-filter channels;
said pre-filter further comprises:
- a downstream filter channel; and
  - downstream pre-filter channels adapted to accommodate said target cells, wherein a respective first end of said upstream pre-filter channels is in fluid connection with said upstream filter channel, a respective second end of said upstream pre-filter channels is in fluid connection with said downstream filter channel, a respective first end of said downstream pre-filter channels is in fluid connection with said downstream filter channel and a respective second end of said downstream pre-filter channels is in fluid connection with said first flow input channel of said upstream microfluidic device; and
- inducing said flow comprises inducing said flow of said biological sample in said upstream filter channel of said upstream microfluidic device between said first end and said second end of said upstream filter channel.

7. The method according to claim 1, wherein inducing said flow comprises inducing an oscillating flow of said biological sample back and forth between said first end and said second end of said flow channel.

8. The method according to claim 1, wherein inducing said flow comprises inducing a circular flow of said biological sample between said first end and said second end of said flow channel and through a fluid connector interconnecting said first end and said second end of said flow channel.

9. The method according to claim 1, wherein monitoring said cell channels comprises taking at least one image of said first cell channels of said upstream microfluidic device.

10. The method according to claim 1, further comprising:
- applying a fluid medium comprising or constituting a test agent at said first end and/or said second end of said second flow input channel in said downstream microfluidic device;
- monitoring target cells in said second cell channels of said downstream microfluidic device; and
- determining a phenotypic response of said target cells to said test agent based on said monitoring of target cells in said second cell channels of said downstream microfluidic device.

11. The method according to claim 10, wherein
said substrate of said downstream microfluidic device has multiple sets of second cell channels adapted to accommodate said target cells;
each set of said multiple sets having a respective second flow input channel, having a respective first end in fluid connection with a respective first fluid port and a respective second end in fluid connection with a respective second fluid port or a common second fluid port;
each set of said multiple sets having a respective second flow output channel in fluid connection with a respective second output fluid port or a common second output fluid port; and
applying said fluid medium comprises applying said fluid medium comprising or constituting said test agent in a first fluid port of a first set of said multiple sets and applying a fluid medium lacking said test agent or comprising or constituting another test agent in a first fluid port of a second set of said multiple sets;
monitoring said target cells comprises monitoring target cells in said second cell channels of said first set and target cells in said second cell channels of said second set; and
determining said phenotypic response comprises determining said phenotypic response of said target cells to said test agent based on said monitoring of target cells in said second cell channels of said first set and of target cells in said second cell channels of said second set.

* * * * *